United States Patent
Gokaraju et al.

(10) Patent No.: US 8,226,989 B2
(45) Date of Patent: Jul. 24, 2012

(54) ANTI-ADIPOCYTE FATTY ACID-BINDING PROTEIN (AP2), ANTI-FLAP AND ANTI-CYSLT1 RECEPTOR HERBAL COMPOSITIONS

(75) Inventors: Ganga Raju Gokaraju, Andhra Pradesh (IN); Rama Raju Gokaraju, Andhra Pradesh (IN); Golakoti Trimurtulu, Andhra Pradesh (IN); Sivaramakrishna Chillara, Andhra Pradesh (IN); Krishanu Sengupta, Andhra Pradesh (IN); Kiran Bhupathiraju, Andhra Pradesh (IN)

(73) Assignee: Laila Impex, Vijayawada, IN (US)

( * ) Notice: Subject to any disclaimer, the term of this patent is extended or adjusted under 35 U.S.C. 154(b) by 323 days.

(21) Appl. No.: 12/477,643

(22) Filed: Jun. 3, 2009

(65) Prior Publication Data
US 2009/0298941 A1 Dec. 3, 2009

Related U.S. Application Data

(60) Provisional application No. 61/058,271, filed on Jun. 3, 2008.

(51) Int. Cl.
*A61K 36/00* (2006.01)
(52) U.S. Cl. .................................................... 424/725
(58) Field of Classification Search ........................ None
See application file for complete search history.

(56) References Cited

U.S. PATENT DOCUMENTS

| | | | |
|---|---|---|---|
| 6,274,177 B1 * | 8/2001 | Wu et al. ........................ 424/756 |
| 2005/0123559 A1 * | 6/2005 | Majeed et al. ............ 424/195.18 |
| 2005/0220913 A1 * | 10/2005 | Ponnapalli et al. ........... 424/777 |
| 2006/0040000 A1 | 2/2006 | Gokaraju et al. |
| 2009/0181110 A1 * | 7/2009 | Balunas et al. ............... 424/725 |

FOREIGN PATENT DOCUMENTS

| JP | 10072357 A | 3/1998 |
|---|---|---|
| JP | 2005298429 A * | 10/2005 |

OTHER PUBLICATIONS

Ghangale et al. Evaluation of Aegle Marmelos (BAEL) for Anti-Inflammatory Activity in Rats; Journal of Bombay Veterinary College; Jan. 2008, vol. 16, Issue 1, one page Abstract.*
Visvabharati, C. 2000, TKDL Translation, 2 pages.*
Sailer et al.—Acetyl-11-Keto-Beta-Boswellic Acid (AKBA): Strucutre Requriements for Binding and 5-Lipdxygnease Inhibitory Activity; Br. J. Pharmacol., Feb. 1996, 117(4) Abstract).*

(Continued)

*Primary Examiner* — Patricia Leith
(74) *Attorney, Agent, or Firm* — Kramer / Amado, P.C.

(57) ABSTRACT

Herbal compositions having anti-adipocyte fatty acid-binding protein (aP2), anti-5-lipoxygenase-activating protein (FLAP) and anti-Cysteinyl Leukotriene (CysLT)-1 receptor expression activity contain an extract of *Boswellia serrata*. More particularly, these herbal compositions comprise an effective amount of an enriched *Boswellia* extract containing from 10% to 99% by weight of 3-0-acetyl-11-keto-$\beta$-boswellic acid; and an effective amount of a second extract selected from the group consisting of an extract of *Aegle marmelos*, an extract of *Zingiber officinale*, an extract of *Garcinia mangostana*, and mixtures thereof. These may be used in dietary supplements or pharmaceutical formulations for controlling diseases associated with or related to inflammation. These diseases in particular include respiratory disorders such as asthma, allergic rhinitis, hay fever, type-1 hypersensitivity and mild allergies. The compositions can also be useful for skin care.

32 Claims, 13 Drawing Sheets

OTHER PUBLICATIONS

Fenech et al., Pharmacogenetics of asthma, J Clinical Pharmacol, 53, 2000, pp. 3-15 (Great Britain).

Knight et al., Protease-activated receptors in human airways: Upregulation of PAR-2 in respiratory epithelium form patients with asthma, J Allergy Clin Immunol, vol. 108, No. 5, Nov. 2001, pp. 797-803 (Great Britain).

Murali et al., Plant-Based Formulation for Bronchial Asthma: A Controlled Clinical Trial to Compare its Efficacy with Oral Salbutamol and Theophylline, www.karger.com/res, Respiration 2006; 73:457-463(www.karger.com/res).

Peres et al., Trioxygenated Naturally Occurring Xanthones, Pythochemistry, vol. 44, No. 2, 1997, pp. 191-214 (Printed in Great Britain).

Peres et al., Tetraoxygenated naturally occurring xanthones, Pythochemistry, vol. 55, (2000) pp. 683-710 (www.elsevier.com/locate/phytochem).

Peters-Golden et al., 5-Lipoxygenase and FLAP,Prostaglandins, Leukotienes and Essential Fatty Acids 69 (2003) pp. 99-109 (www.elsevier.com/locate/plefa).

Sastri, The Wealth of India, Council of Scientific & Industrial Research (New Delhi) 1956, pp. 103-105.

Shiota et al., Pathopysiological role of mast cells in collagen-induce arthristis: Study with a cysteinyl leukotriene receptor antagonist, montelukast, European Journal of Pharmacology 548, 2006, 158-166 (www.elsevier.com/locate/ejphar).

Srivastava KC: Ginger (*Zingiber officinale*) in rheumatism and muscular skeletal disorders. Med Hypoth (1992) 39: 342-348.

Tjendraputra et al., Effect of Ginger Constituents and Synthetic Analogues on Cyclooxygenase-2 Enzyme in Intact Cells, Bioorganic Chemistry 29, 2001, pp. 156-163 (www.idealibrary.com).

Van Oosterhout et al., Role of Cytokines in Bronchial Hyperresponsiveness, Pulmonary Pharmacology, 1993, 6 pp. 225-236.

Savithramma et al., Ethnobotanical survey of plants used to treat asthman in Andhra Pradesh, India, Journal of Ethnopharmacology 113(2007) 54-61.

Ulbricht et al., Boswellia: An Evidence-Based Systematic Review by the Natural Standard Research Collaboration. Journal of Herbal Pharmacotherapy, vol. 4(3) 2004.

Arul et al., Mechanisms of the contractile effect of the alcoholic extract of *Aegle marmelos* Corr, on isolated guinea pig ileum and tracheal chain. Phytomedicine 11 (2004) 679-683.

Manthana Bhairava: Anandakandah-Edited with Tamil Translation by S.V. Radhakrishna Sastri, T.M.S.S.M. Libray, Tanjore, Madras, Edn 1st 1952 p. 269. Formulation ID: RS 13/336E. Formulation Name: Udvartan Rasyan.

Mohammad Najmul Ghani Kahn et al., vol. III (20th century AD), Nadeem Yunus Printer/Sheihk Mohd Basheer & Sons, Lahore, 1926 AD p. 409. Formulation ID JA6/383A. Formulation Name Dawa Kundur.

Mohammad Asam Kahan et al., vol. I (19th centrury AD) Matba Nizami, Kanpur, 1896 AD p. 334. Formulation ID; MH3/495H. Formulation Name: Dawa Baloot.

Mohammad Najmul Ghani Khan et al., (20th centrury AD), Munshi Nawal Kishore, Lucknow, (Second edition) 1928 AD p. 37. Formulation ID: NA4/153. formulation Name: Afshara Barai Sual Wa Zeequnnaias.

Lankapatiravana et al., Edited and translation by Indradeva Tripathi, Krishnadas Academy, Varanasi, Edn, 1st 1995 p. 117. Formulation ID: AK14/31513. Formulation Name: Nasika Rogahara Yoga-2.

Govt of India; Sahastrayoga—Tanslated by D.V. Panditarao: Central Council for Research in Ayurveda & Siddha, New Delhi, 1990 p. 63. Formulation ID VS/2964, Formulation Name: Panalaveradikasayah.

Vangasena et al., Commentator Shaligram Vaisya. Edited Shankar Ialji Jain et al., Bombay Edn. 1996 p. 910. Formulation ID: AK11/4080. Formulation Name: Nirgundyadi Udvartna.

Mohammad Azam Khuan et al., vol. I (19th century AD) Matba Nizami, Kanpur 1896 AD p. 129-130. Formulation ID: MH3/72. Formulation Name: Adrak.

Kali Dasa et al., with Hindi translation. Central Council for Reseaerch in ayrveda & Siddha, Gov't of India, New Delhi, Edn. 2005. p. 133. Formulation ID RS14/558. Formulation Name: Valli Palitahara Yoga,.

Cudamani et al., Edited by Jivaramakalidasa Sastri, Part 4, Chaukhamha Publishers, Varanis, Edn 1st 1992 p. 286.

Bharata Bhaisajya Ratnaka. vol. III. B. Jain Publishers, New Delhi, Edn. 2nd Reprit, Aug. 1999 p. 267. Formulation ID: RG/942. Formulation Name: Patoladikvathah(38).

Rasayoga Sagara, vol. I, Krishandas Academy, Varansai Edn. Reprint, 1999. p. 306. Formulation ID SJ/715B. Formulation Name: Kitimarirasah-2.

Wada et al., Biocativities of Boswellia gum resin. Aroma Research (2006), 7(3), 234-241. CAS Abstract.

Sharma et al, "Phytochemical profile of Boswellia serrata:an overview". Pharmacognosy Reviews (2007) 1(1), 137-142. CAS Absract.

* cited by examiner

ANTI-ADIPOCYTE FATTY ACID-BINDING PROTEIN (AP2), ANTI-FLAP AND ANTI-CYSLT1 RECEPTOR HERBAL COMPOSITIONS

CROSS REFERENCE TO RELATED APPLICATIONS

Applicants herein incorporate by reference in its entirely the U.S. Provisional Application filed on Jun. 3, 2008, entitled ANTI-ADIPOCYTE FATTY ACID-BINDING PROTEIN (aP2), ANTI FLAP AND ANTI-CYSLT1 RECEPTOR HERBAL COMPOSITIONS FOR PREVENTING AND CONTROLLING ASTHMA in the name of GOKARAJU et al.

FIELD OF THE INVENTION

The invention relates to herbal compositions comprising a 3-O-acetyl-11-keto-β-boswellic acid (AKBA) enriched extract of *Boswellia serrata*. The present invention further relates to dietary supplements or pharmaceutical formulations containing these herbal compositions for immuno modulation or controlling diseases related to inflammation. The herbal compositions can also be useful for skin care.

BACKGROUND OF THE INVENTION

The inflammatory processes are known to be triggered by increased metabolic activity of arachidonic acid. Arachidonic acid diverges down into two main pathways during this process, the cyclooxygenase (COX) and lipoxygenase (LOX) pathways. The COX pathways lead to prostaglandins and thromboxane production and the LOX pathways leads to leukotrienes (LTS) and hydroxyl eicosatetraenoic acid (HETEs). These classes of inflammatory molecules exert profound biological effects, which enhance the development and progression of human cancers. Inhibition of 5-lipoxygenase indirectly reduces the expression of TNF-α. Both 5-Lipoxygenase and TNF-α therefore, are the target enzymes useful for identifying inhibitors, which have the potential to cope with a variety of inflammations and hypersensitivity-based human diseases including asthma, arthritis, bowel diseases such as ulcerative colitis and circulatory disorders such as shock and ischemia.

Asthma is the most common disease of diffuse airway inflammation caused by variety of stimuli and characterized by reversible and recurrent attacks of breathlessness and wheezing. US Census Bureau; Population Estimates and International Data Base, 2004 estimated that globally 373,847,408 people suffer from Asthma. An approximate 30.2 million American citizens have been diagnosed with asthma. Children and teenagers from 5-17 years of age have the highest prevalence rates. In 2004, 14.01% children were diagnosed with asthma.

The pathophysiology of asthma consists of chronic inflammation of airways accompanied by a degree of airway remodeling, which results in decreased airway caliber. Accumulation of inflammatory cells in to the airway lining, together with inflammatory cascade contribute to the development of edema, hyper-secretion of mucus and epithelial cell shedding which results in airway plugging. The elevated IgE levels results in hypersensitivity.

The enriched *Boswellia* composition used in various exemplary embodiments of the present invention contains a unique blend of triterpenes, selectively enriched with the most active boswellic acid called 3-O-acetyl-11-keto-β-boswellic acid (AKBA) and characterized by a lack of significant quantities of the components present in regular *Boswellia serrata* extracts except AKBA, which is a minor component in regular extracts and a major component in the enriched *Boswellia* composition. The components present in regular extracts are 1) β-boswellic acid, 2) 3-O-acetyl-β-boswellic acid, 3) 11-keto-β-boswellic acid, 4) 3-O-acetyl-11-keto-β-boswellic acid. 5) 9-ene-β-boswellic acid, 6) 3α-hydroxyurs-9,11-diene-24-oic acid, 7) 2α,3α-hydroxyurs-12-ene-24-oic acid. The components of the unique *Boswellia* enriched product used in various exemplary embodiments of the present invention are 1) 3-O-acetyl-11-keto-β-boswellic acid, 2) 3-O-acetyl-9(11)-dehydro-β-boswellic acid, 3) 3-O-acetyl-11-keto-β-amirin, 4) 3-O-acetyl-11-keto-α-boswellic acid. An enriched extract containing more than 30% 3-O-acetyl-11-keto-β-boswellic acid is preferably used in various exemplary embodiments of the present invention. Extracts enriched to higher concentration of AKBA may also be used. A suitable enriched extract may be obtained from Laila Nutraceuticals, India, under the brand name 5-Loxin®.

*Aegle marmelos* (Bael) is a medium sized tree that grows up to 40 ft. It is native to Central and Southern India, Pakistan, Bangladesh, and Burma. The flesh of the *Aegle marmelos* fruit is eaten raw or processed into drinks or flavoring. Unripe pulp is used to treat diarrhea and dysentery. All other parts of the plant are used for a wide variety of medicinal purposes. Fruit or leaf or root or bark extracts or mixtures thereof are used in various exemplary embodiments of the present invention.

*Zingiber officinale* (Ginger) has been used as a treatment for nausea, diarrhea and epigastric and joint pains in Ayurvedic and traditional Chinese medicine. Ginger has anti-histaminic activity. Ginger's oleoresin constituents have potent inhibitory effects on the biosynthesis of pro inflammatory prostaglandins and leukotrienes. Shogaol and Paradol inhibit COX-2 activity and Gingerol inhibits 5-LOX enzyme activity. In an uncontrolled trial, all seven arthritis patients treated with half gram of powdered ginger per day reported pain relief and decreased signs of inflammation. Ginger root extracts standardized to 5-15% gingerols are used to prepare this composition. Extracts standardized to other concentrations and other components could also be used for making the present inventive compositions.

*Garcinia mangostana* L belongs to the Guttiferae family. It is commonly known as Mangosteen. Mangosteen is a slow-growing tropical, evergreen tree and can attain 6-25 m in height with leathery glabrous leaves. The tree is mainly found in India, Myanmar, Sri Lanka and Thailand. The edible fruits of this plant are considered to be one of the best of all tropical fruits. In the ayurvedic system of medicine, the fruit hull of the plant finds wide application, mainly as an anti-inflammatory agent and in the treatment of diarrhea. *Garcinia mangostana* alcohol extracts or hydroalcohol extracts standardized to α-mangostin are used in various exemplary embodiments of the present invention. However *Garcinia mangostana* extracts selectively enriched in γ-mangostin may also be used.

Various exemplary embodiments of the present invention provide pharmaceutical or dietary supplement compositions comprising *Boswellia serrata* extract selectively enriched in 3-O-acetyl-11-keto-β-boswellic acid (AKBA) and extracts of *Aegle marmelos* for improved therapeutic effect in the prevention, treatment and control of asthma and other inflammatory diseases.

Further exemplary embodiments provide medicinal compositions comprising an effective amount of an enriched *Boswellia* extract containing from 10% to 99% by weight of 3-0-acetyl-11-keto-β-boswellic acid; and an effective amount of a second extract selected from the group consisting of an extract of *Aegle marmelos*, an extract of *Zingiber officinale*, an extract of *Garcinia mangostana*, and mixtures thereof.

Further embodiments of the invention are directed to methods of ameliorating the effects of adipocyte fatty acid binding protein (aP2) mediated disease conditions by administering an effective amount of a composition including *Boswellia serrata* extract selectively enriched in 3-O-acetyl-11-keto-β-boswellic acid (5-Loxin), in combination with *Aegle marmelos* extract, *Zingiber officinale, Garcinia mangostana*, or mixtures thereof for improved therapeutic effect.

Additional embodiments of the invention are directed to methods of ameliorating the effects of adipocyte fatty acid binding protein (aP2) mediated disease conditions by administering an effective amount of a composition including *Boswellia serrata* extract selectively enriched in 3-O-acetyl-11-keto-β-boswellic acid (5-Loxin) and *Aegle marmelos* extract, optionally in combination with *Zingiber officinale* and/or *Garcinia mangostana* for improved therapeutic effect.

Still other embodiments of the present invention are directed to methods of ameliorating the effects of 5-Lipoxygenase Activating Protein (FLAP) and Cysteinyl Leukotriene (Cys LT)-1 mediated disease conditions by administering an effective amount of a composition comprising *Boswellia serrata* extract selectively enriched in 3-O-acetyl-11-keto-β-boswellic acid such as 5-Loxin and extracts of *Aegle marmelos*, optionally in combination with *Zingiber officinale* and *Garcinia mangostana* for improved therapeutic effect.

Further embodiments of the present invention provide efficacious compositions comprising *Boswellia* extract selectively enriched in AKBA, extracts/fractions/pure isolates selected from *Aegle marmelos*, and one or more extracts/fractions/pure isolates selected from *Zingiber officinale, Garcinia mangostana*, optionally in combination with one or more pharmaceutically and nutraceutically acceptable additives or excipients.

Additional embodiments of the present invention provide compositions comprising *Boswellia* extract selectively enriched in AKBA, extracts/fractions/pure isolates selected from *Aegle marmelos*, and one or more extracts/fractions/pure isolates selected from *Zingiber officinale, Garcinia mangostana*, optionally in combination with one or more other known anti-inflammatory or anti-asthma or immune modulating herbs.

SUMMARY

The present application discloses medicinal compositions comprising an effective amount of an enriched *Boswellia* extract containing, from 10% to 99% by weight of 3-0-acetyl-11-keto-β-boswellic acid; and an effective amount of a second extract selected from the group consisting of an extract of *Aegle marmelos*, an extract of *Zingiber officinale*, an extract of *Garcinia mangostana*, and mixtures thereof. In various embodiments, the second extract is an ethanol or hydroalcohol extract.

The present application also discloses anti-adipocyte fatty acid-binding protein (anti-aP2), anti 5-Lipoxygenase Activating Protein (anti-FLAP) and anti-Cysteinyl Leukotriene (anti-CysLT)-1 receptor pharmaceutical, nutraceutical and dietary supplement compositions comprising *Boswellia serrata* extract selectively enriched in 3-O-acetyl-11-keto-β-boswellic acid including but not limited to 5-Loxin and extracts of *Aegle marmelos*, optionally containing one or more of extracts/fractions/pure isolates of *Zingiber officinale,* *Garcinia mangostana* for the prevention, treatment and control of inflammation and asthma. The composition can also be useful for skin care.

DETAILED DESCRIPTION

Figure 1:
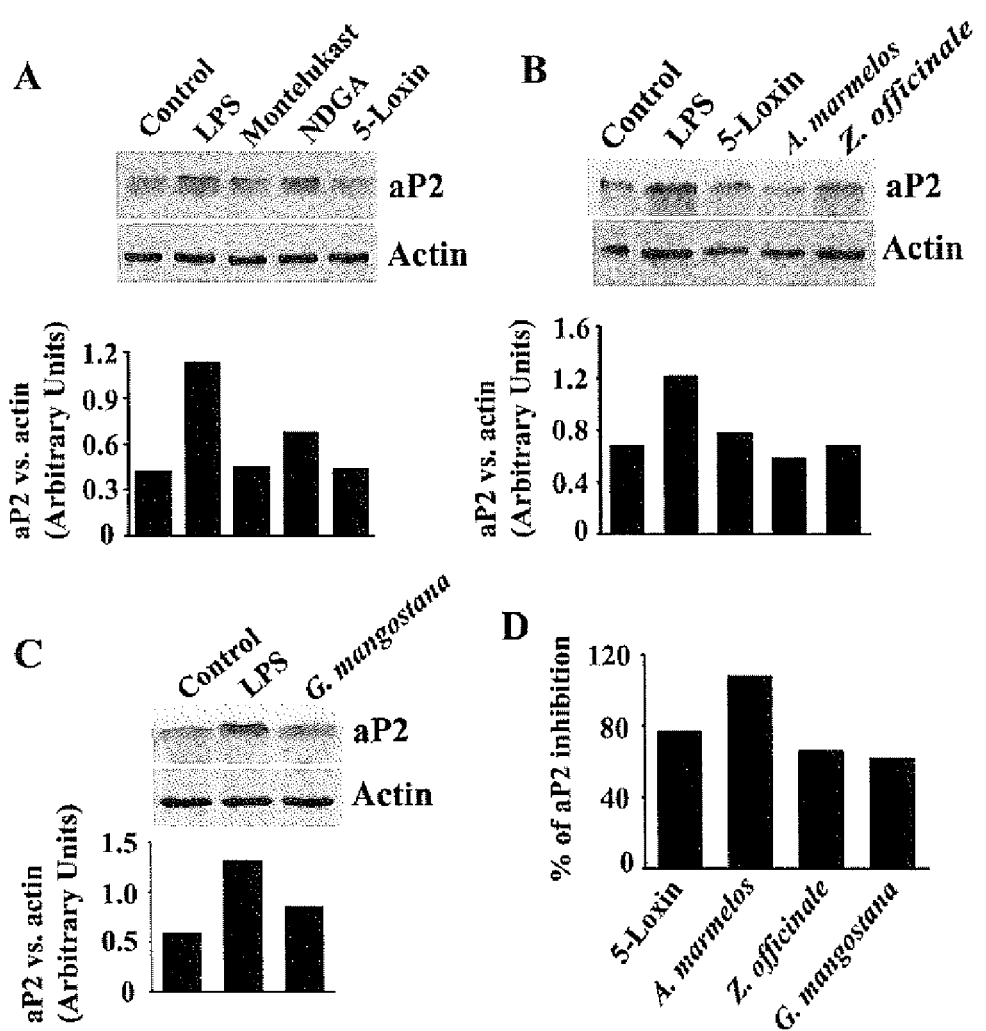
FIG. 1A is a representative immune blot showing 5-Loxin-induced inhibition of aP2 protein in human monocytes THP-1 cells derived macrophages. THP-1 cells were differentiated to macrophages by Phorbol myristate acetate. Macrophage cells were treated with 100 ng/ml of LPS in either 0.1% DMSO (control) treated cells or pre-treated with Montelukast (1 μM), or NDGA (10 μM) or 5-Loxin® (5 μg/ml). The aP2 protein expression was specifically detected in cell lysates by Western-immunoblots and normalized with the expression of actin protein (lower panel).
FIG. 1B is a representative immuno blot showing inhibition of aP2 protein in human monocytes THP-1 cells derived macrophages by 5-Loxin, *Aegle marmelos* and *Zingiber officinale*.
FIG. 1C is immunoblot showing *Garcinia mangostana*-induced inhibition of aP2 protein in human monocytes THP-1 cells derived macrophages.
FIG. 1D is bar diagrammatic representation of the comparative percentage inhibition of aP2 protein by 5-Loxin and extracts of *Aegle marmelos, Zingiber officinale* and *Garcinia mangostana*.

Asthma is a complex chronic inflammatory disease of the airways that involves the activation of many inflammatory and structural cells, all of which release inflammatory mediators that result in the typical patho-physiological changes. A number of inflammatory mediators, such as kinins, cytokines, eicosanoids, enzymes and adhesion molecules act on specific targets leading to the local release of other mediators from leukocytes, and also attract leukocytes to the site of inflammation. Leukotrienes, especially, play key role in lung function and diseases and are responsible for a number of the effects of asthma and allergies. Asthma can be controlled effectively by inhibiting the formation of inflammatory mediators, such as eicosanoids, prostaglandins and leukotrienes, which are produced primarily from arachidonic acid that has been released from the cell membranes.

Cytokines play an integral role in the coordination and persistence of the inflammatory process in the chronic inflammation of the airways in asthma. Among these, pro-inflammatory cytokines such as TNF-α, IL-1β, IL-6, GM-CSF and CD4−. Th2 subset derived IL-4, IL-5 and IL-13 lymphokines are considered as the key factors of immunopathogenesis of asthma. They are capable of inducing many of the pro-inflammatory effects characteristic of this disease and are being recognized as important targets for treatment. TNF-α is a central mediator of airway inflammation and bronchial hyper responsiveness in asthma.

Adipocyte fatty acid binding protein (aP2) is a member of large family of fatty acid binding proteins (FABPs) with distinct patterns of tissue distribution. The aP2 expressed in adipocytes regulates systemic glucose and lipid metabolism. The aP2 protein is also expressed by airway epithelial cells and up-regulated following stimulation of epithelial cells with Th2 cytokines. Recent studies suggest that aP2 plays an important role in regulation of immune responses in bronchial epithelial cells, the site of allergic manifestations in asthma; in addition, aP2-deficient mice are resistant to develop allergic airway inflammation. The infiltration of leukocytes, especially eosinophils into the airways is highly dependent on aP2 function. The aP2 protein regulates allergic airway inflammation and provides a key link between arachidonic acid metabolism and asthma. Hence blocking aP2 function is a novel approach to therapeutic strategy of asthma.

The 5-Lipoxygenase activating protein, also known as FLAP, is an enzyme necessary for the activation of 5-lipoxygenase and therefore for the production of leukotrienes. It is bound to the nuclear membrane. Hence blocking or down regulating the FLAP is also a novel approach to therapeutic strategy of asthma.

Cysteinyl-LTs are key inflammatory mediators that play important roles in the pathophysiology of asthma, allergic rhinitis, and other inflammatory conditions. The cysteinyl-leukotrienes (LTC4, LTD4 and LTE4) act at their cell-surface receptors CysLT1 and CysLT2 on target cells to contract bronchial and vascular smooth muscle, to increase permeability of small blood vessels, to enhance secretion of mucus in the airway and gut, and to recruit leukocytes to sites of inflammation. As cysteinyl leukotrienes (CysLTs) contribute to many of the symptoms of asthma, blocking cysteinyl leukotrienes (CysLTs) or their receptor function is a novel approach to therapeutic strategy of asthma. It was also proved that inhibition of CysLT1 by inhibiting TNF-α production can be useful for treatment of Arthritis.

Th1 and Th2 cells are important in regulation of immune responses. The Th1 cells and the pathway they dominate are heavily reliant on IFNγ, where as the Th2 cells are more heavily reliant on interleukin-4 (IL-4). Asthma is a complex inflammatory disease characterized by bronchial hyperresponsiveness and airway inflammation. The CD4+ lymphocytes with Th2 cytokine pattern play a pivotal role in the pathogenesis of asthma, especially airway hyperresponsiveness. The Th1 cells are required to for recruitment of adoptively transferred Th2 cells to the lung. Under the conditions of asthma the Th2 vs Th1 ratio is in favour of Th2. The Th2/Th1 balance is thus an important factor, which has profound implication on the conditions associated with inflammation, especially respiratory disorders. The IL-4/IFNγ ratio in the lung tissue lysates is a measure of Th2/Th1 balance.

Based on the above information, the inventors have conducted several cell based in vitro anti-inflammatory studies, particularly anti-asthma studies on many extracts or enriched extracts including those derived from *Boswella serrata*, *Aegle marmelos* (Bael). *Garcinia mangostana* (Mangosteen) and *Zingiber officinale* (Ginger). These studies have un-expectedly indicated potent anti-aP2 activity for these extracts. Further unexpectedly, the compositions comprising the extracts derived from these plants also showed potent anti-TNF-α activity, anti-aP2 activity, anti-FLAP and anti-CysLT1 receptor activities.

The inventors assessed the effect of *Boswellia serrata* extract enriched to 30% 3-O-acetyl-11-keto-β-boswellic acid (AKBA) (5-Loxin) and extracts of *Aegle marmelos*, *Zingiber officinale* and *Garcinia mangostana* on adipocyte fatty acid-binding protein aP2 expression in human monocytes-macrophage cells in a cell based in vitro model. In this experiment, THP-1 human monocyte-macrophage cells were pre-treated with 5 or 10 µg/ml of each ingredient for 2 h and thereafter printed with LPS to induce the inflammatory response. The cellular proteins were extracted by cell lysis buffer and subjected to Immuno-Western blot to detect the modulation of expression of aP2 protein. The data has shown unexpectedly that 5-Loxin could able to potently inhibit the LPS induced aP2 expression in THP-1 human monocyte-macrophage cells (FIG. 1A). The extracts of *Aegle marmelos*, *Zingiber officinale* and *Garcinia mangostana* also showed potent aP2 expression inhibitory activity (FIGS. 1B and 1C). The comparative inhibition of aP2 by 5-Loxin, extracts of *Aegle marmelos*, *Zingiber officinale* and *Garcinia mangostana* is summarized in FIG. 1D.

Figure 2:
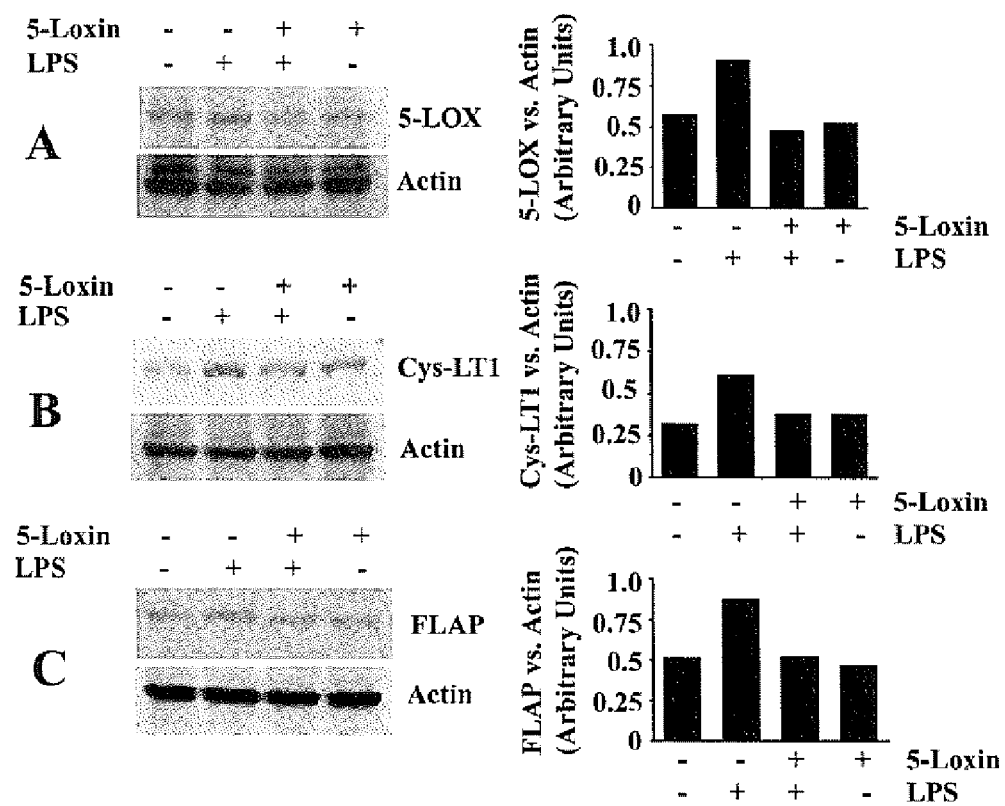
FIG. 2 depicts representative immuno blots showing 5-Loxin-induced inhibition of 5-Lipoxygenase (A), Cysteinyl LT1 (B) and FLAP (C) expressions in human monocytes THP-1 cells. In each respective panel, bar diagram represent the normalized densitometric values (in arbitrary units).

The effect of 5-Loxin on the other key intermediary proteins of arachidonic acid mediated inflammatory pathway was assessed in LPS induced-THP-1 human-monocyte-macrophage cells in vitro by pre-treating THP-1 cells with 5-Loxin and thereafter primed the cells with LPS to induce the inflammatory response. The cellular proteins were extracted by cell lysis buffer and subjected to immuno-western blot to detect the modulation of the expression of 5-LOX and Cysteinyl LT1 proteins. 5-Loxin significantly down regulated 5-LOX and CysLT1 expressions in LPS induced THP-1 human-monocyte-macrophage cells (FIGS. 2A and 2B).

The inventors also examined the effect of 5-Loxin on LPS induced expression of the 5-lipoxygenase-activating protein (FLAP), which is critical for leukotriene synthesis in mononuclear phagocytes. Prolonged exposure to the bacterial component, lipopolysaccharide (LPS), increased FLAP gene transcription, mRNA expression, and protein expression in the human monocyte-like THP-1 cell line. Unexpectedly, 5-Loxin significantly down regulated the expression of FLAP compared to that in the untreated control group (FIG. 2C).

An in vivo experiment was conducted to check if the anti-aP2 effects shown, by 5-Loxin in vitro are rightly translated into in vivo effects in a Sephadex induced asthma model in Sprague-Dawley rats. In this study airway inflammation was induced in Sprague-Dawley rats by administering Sephadex as a suspension in sterile saline for 3 days through intrathoracic route. The control group animals were administered with sterile saline. The study animals were supplemented with 5-Loxin for ten days prior to the asthma induction. Animals were sacrificed 48 h after saline or Sephadex challenge; blood and lung tissue samples were collected from respective animals. Pro-inflammatory cytokines such as TNF-α and IL-4 were measured in serum and protein lysates prepared from lung tissues by specific and sensitive ELISA kits (R&D Systems, USA). The results are summarized in FIG. 3. The serum and lung tissue levels of TNFα and IL-4 are significantly enhanced in the sephadex treated animals compared to those in the naïve group. These levels have been significantly reduced by 5-Loxin treatment. These results supports the in vitro aP2 inhibition shown by 5-Loxin in THP-1 human monocyte-macrophage cells.

Figure 4:
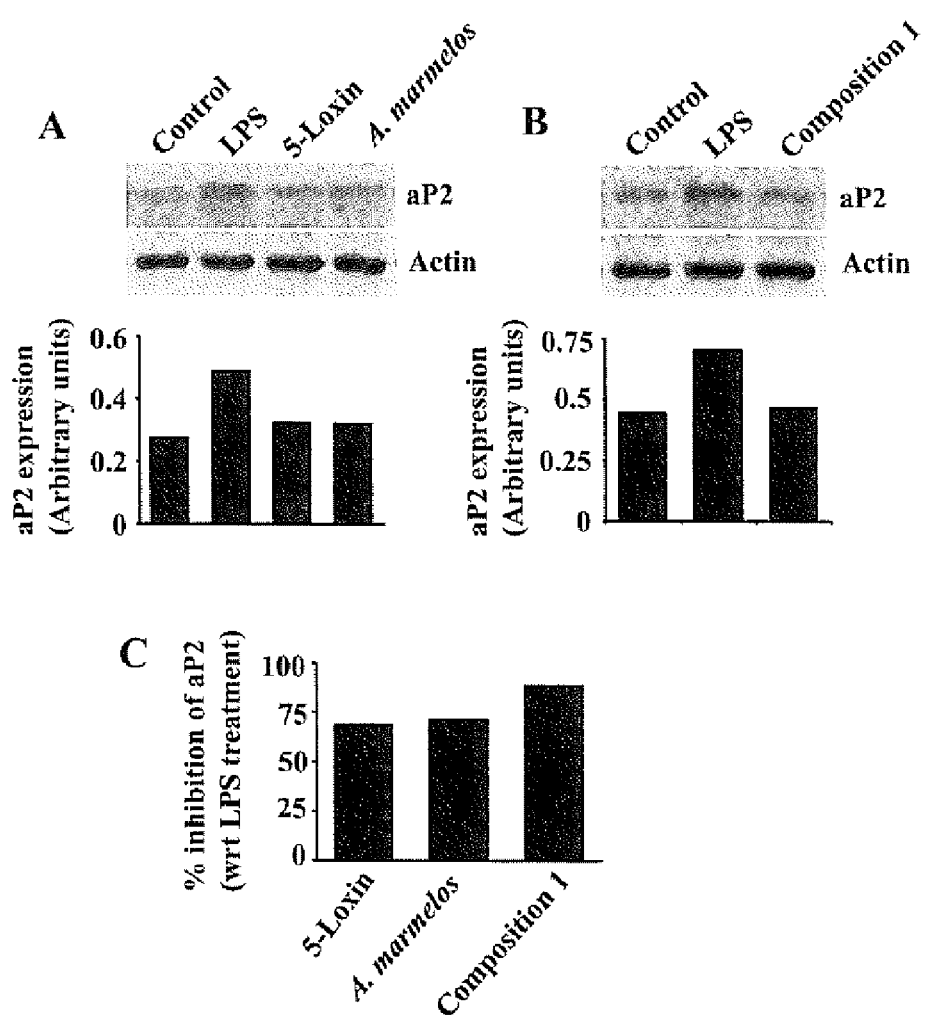
FIG. 4 exhibits synergistic inhibition of aP2 expression by Composition-1 compared to its individual ingredients. Panel A & B show 5-Loxin, bael and composition 1 inhibit aP2 expression in LPS induced THP-1 human monocytes-macrophage cells. The aP2 protein expressions were measured densitometrically, normalized with actin expression and represented as bar diagrams. Panel C shows bar diagrammatic representation on comparative data of percent inhibition in aP2 expression in THP-1 cells treated with composition-1 and its individual ingredients.
Figure 5:
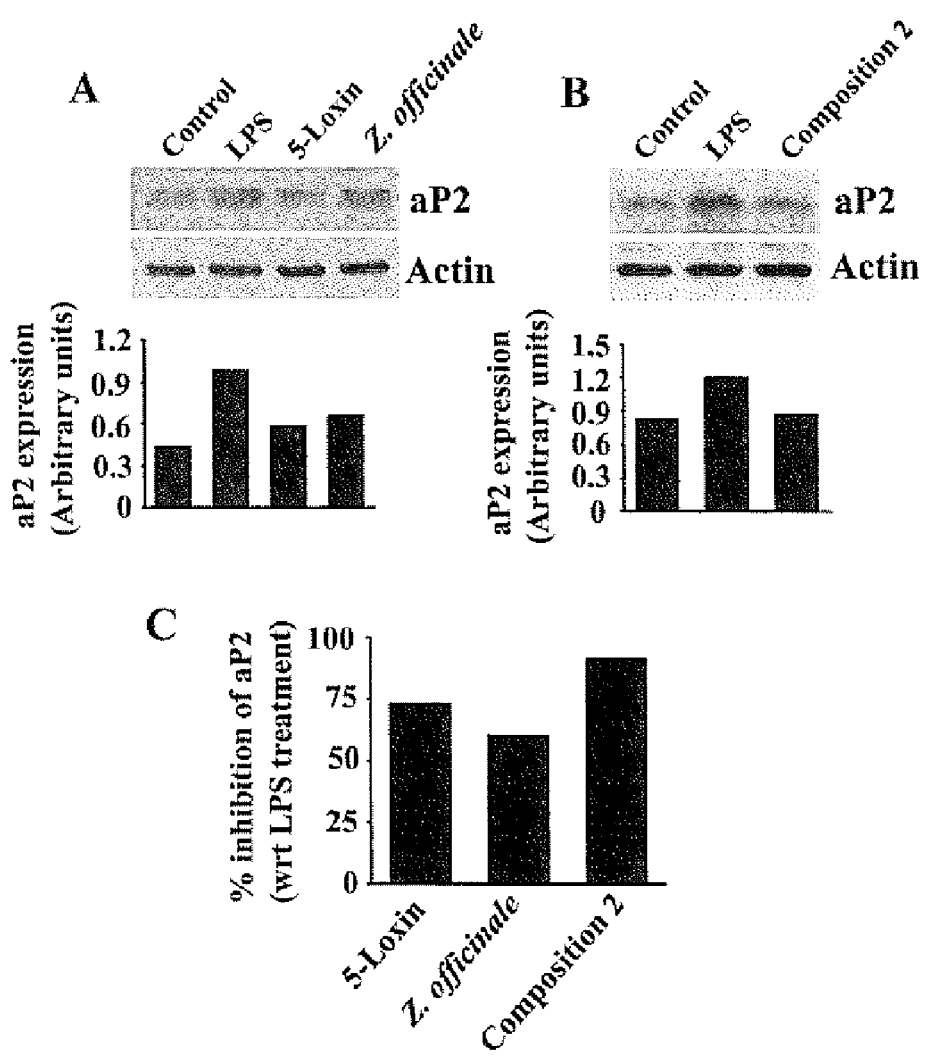
FIG. 5 exhibits synergistic inhibition of aP2 expression by Composition-2 compared to its individual ingredients. Panel A & B show 5-Loxin, ginger and composition-2 inhibit aP2 expression in LPS induced THP-1 human monocytes-macrophage cells. aP2 protein expressions were measured densitometrically, normalized with actin expression and represented as bar diagrams. Panel C shows bar diagrammatic representation on comparative data of percent inhibition in aP2 expression in THP-1 cells treated with composition-2 and its individual ingredients.
Figure 6:
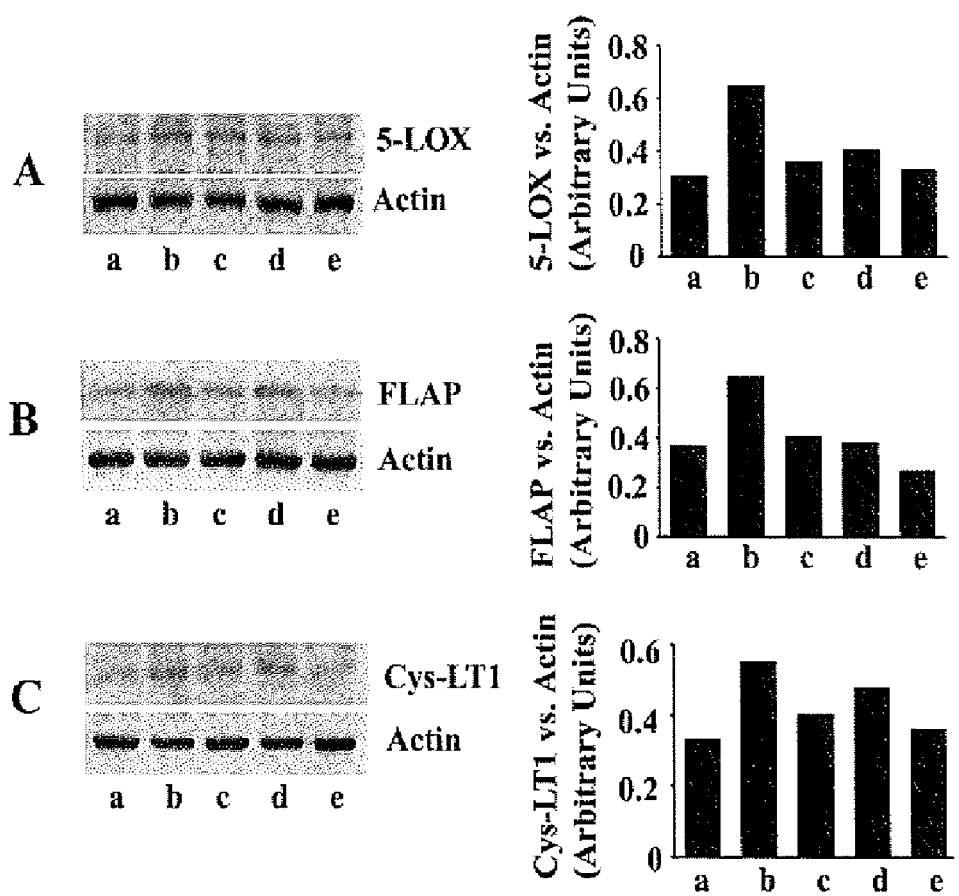
FIG. 6 depicts representative immunoblots showing the inhibition of 5-Lipoxygenase (5-LOX) (A), FLAP (B) and Cys-LT1 (C) protein expression in LPS induced human THP-1 monocytes by composition-1. The immunoblots are shown in the right panel. a, vehicle control; b, LPS; c, 30% AKBA+LPS, d, alcohol extract of Aegle marmelos fruit+LPS and e, composition-1+LPS. The bar diagrams in the side panels represent the normalized densitometric units (in arbitrary units) of respective proteins.
Figure 7:
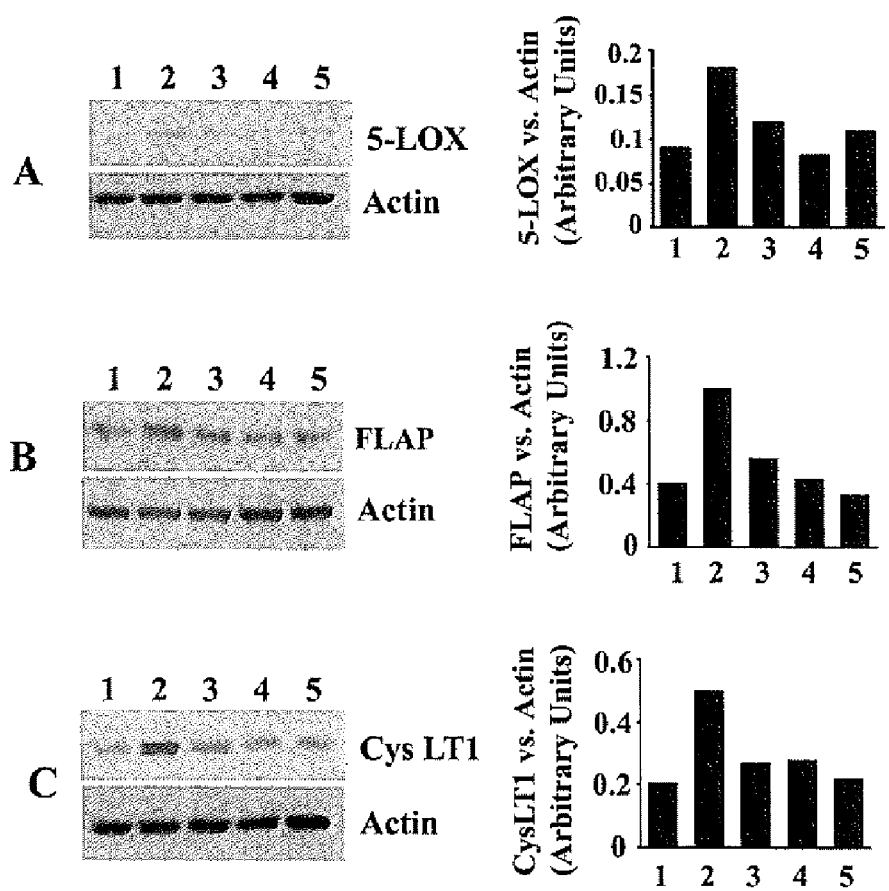
FIG. 7 is representative immunoblots showing synergistic inhibition of 5-LOX (A), FLAP (B) and Cys LT1 (C) protein expression in LPS induced human THP-1 monocytes by composition-2. 1 is vehicle control; 2 represents LPS induction; 3, 4 and 5 represents cells treated with, 10 ug/ml of 5-Loxin®, 10 ug/ml of alcohol extract of Zingiber officinale and 10 ug/ml of composition-2 respectively. The bar diagrams in the side panels represent the normalized densitometric units (in arbitrary units) of respective proteins.

The inventors further explored the possibility of developing synergistic compositions containing 5-Loxin as the base ingredient. Several combinations of the ingredients comprising 5-Loxin and one or more of the extracts derived from *Aegle marmelos*, *Zingiber officinale* and *Garcinia mangostana* were prepared compositions-1 to 10 and a few of them were tested for aP2 expression inhibition activity. A few selected compositions are composition-1 comprising 5-Loxin and extract of *Aegle marmelos*, composition-2, comprising 5-Loxin and extract of *Zingiber officinale* and composition-3, comprising 5-Loxin and extract of *Garcinia mangostana*. The compositions-1 and 2 were tested for aP2 inhibition and both of them unexpectedly showed synergistic inhibition of aP2 protein compared to the corresponding individual ingredients in the composition as shown in FIGS. 4 and 5 respectively for composition-1 and composition-2. These compositions also showed synergistic inhibition of FLAP and CysLT1 as shown in FIG. 6 for composition-1 and as shown in FIG. 7 for the composition-2.

The composition-4 comprising 5-Loxin, (*Aegle marmelos*) Bael and (*Zingiber officinale*) ginger extracts and composition-9 comprising 5-Loxin, bael and (*Garcinia mangostana*) mangosteen extracts also showed significant down regulation of aP2, FLAP and CysLT1 protein expression in LPS induced human THP-1 monocyte cells.

Emerging evidence from experimental and clinical studies suggests that TNF-α plays a major role in the pathogenesis of human asthma, thus emphasizing the significance of TNF-α as an important therapeutic target in this common medical condition. Interleukin-4 (IL-4) is another important marker for asthma. IL-4 mediates important pro-inflammatory functions in asthma including induction of the IgE isotype switch, expression of vascular cell adhesion molecule-1 (VCAM-1), promotion of eosinophil transmigration across endothelium, mucus secretion, and differentiation of T helper type 2 (Th2) lymphocytes leading to cytokine release.

The Adipocyte Fatty acid binding, protein (aP2) plays an important role in the regulation of immune responses in bronchial epithelial cells, the site of allergic manifestations in asthma and infiltration of leukocytes, especially eosinophils into the airways is highly dependent on aP2 function. The inventors thus hypothesized that the above compositions having potent anti-aP2 activity in particular and anti-FLAP and anti-CysLT1 in general could be potential therapeutic agents for the prevention, treatment and control of asthma. The inventors thus conducted animal experiments to check if the potent aP2 activity exhibited by the foregoing compositions is rightly translated into the anti-asthma activity in vivo. As the airway inflammation has been the primary symptom of asthma, the inventors studied the anti-asthma effect of the compositions comprising 5-Loxin and one or more extracts derived from *Aegle marmelos, Zingiber officinale* and *Garcinia mangostana* (compositions-1, 2 and 3) in an airway inflammation model in Sprague-Dawley rats.

Figure 8:
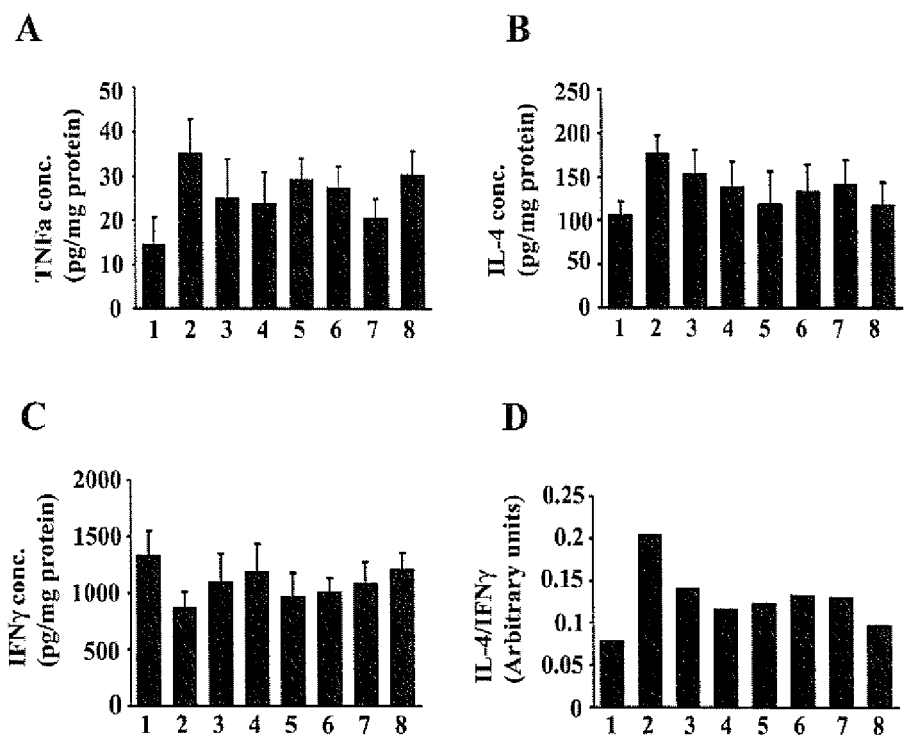
FIG. 8 represents in vivo anti-asthma efficacy of compositions-1, 2 and 3. The bar diagram represents the reduction of TNFα (A), IL-4 (B), IFN-γ (C) in drug supplemented Sprague-Dawley rats in Sephadex LH-20 induced airway inflammatory model. Bar diagrams represent the Th1 and Th2 cytokines in lung tissue protein lysates. Experiment includes, CMC supplemented group challenged with vehicle (1); CMC supplemented group challenged with Sephadex (2); 100 and 200 mg/kg body weight treatment groups of Composition-1 (3 and 4); 100 and 200 mg/kg body weight treatment groups of Composition-2 (5 and 6); 200 mg/kg body weight treatment group of Composition-3 (7); and 5 mg/kg of Montelukast supplemented group (8) challenged with Sephadex. Each bar represents mean±SD (n=6). * represents P<0.05, (vs. Sephadex challenge in CMC fed group). D, represents the bar diagrammatic presentation of the ratio of IL-4 and IFN-γ in each group, as indicated.

Airway inflammation was induced in Sprague-Dawley rats by administering Sephadex as a suspension in sterile saline for 3 days through intratracheal route. The study animals were supplemented with compositions-1, 2 and 3 for ten days prior to the asthma induction. Animals were sacrificed 48 h after saline or Sephadex challenge; blood and lung tissue samples were collected from respective animals. Pro-inflammatory cytokines such as TNF-α and IL-4 were measured in serum and lung tissue lysate by specific and sensitive ELISA kits (R&D Systems, USA). The lung TNF-α and IL-4 levels were highly elevated and IFN-γ level was significantly reduced (FIG. 8) in the sephadex induced Asthma rats (b), compared to the control animals (a). However the treatment with compositions-1, 2 and 3 significantly ameliorated the lung TNF-α (8A) and IL-4 (8B) and IFN-γ (8C) levels towards their normal levels. More importantly, the ratio of lung IL-4/IFN-γ was significantly reduced in all the treatment groups (8D). This data confirmed the anti-aP2 activity exhibited by the said compositions in vitro.

A similar experiment was repeated again with composition-1 comprising 5-Loxin and *Aegle marmelos* (Bael) fruit extract to study its effect on percentage granulocytes in blood, eosinophil percentage in Peripheral blood and percentage granulocytes in Bronchioalveolar Lavage fluid under the conditions of asthma, in addition to further confirm its effects on lung TNF-α, IL-4 and IFN-γ (9C) levels. Further more improved Th2/Th1 cytokine balance derived from IL-4/IFN-γ ratio in composition-1 treated animals substantiates the anti-asthmatic activity of composition comprising 5-Loxin and Bael. The animals of treatment groups were supplemented with composition-1 at 100 mg/kg or 200 mg/kg body weight for ten days prior to the induction of airway inflammation, whereas, the control group of animals was treated with just 10 mL/kg bodyweight of 0.5% CMC (CarboxyMethylCellulose) suspended in water.

Figure 9:
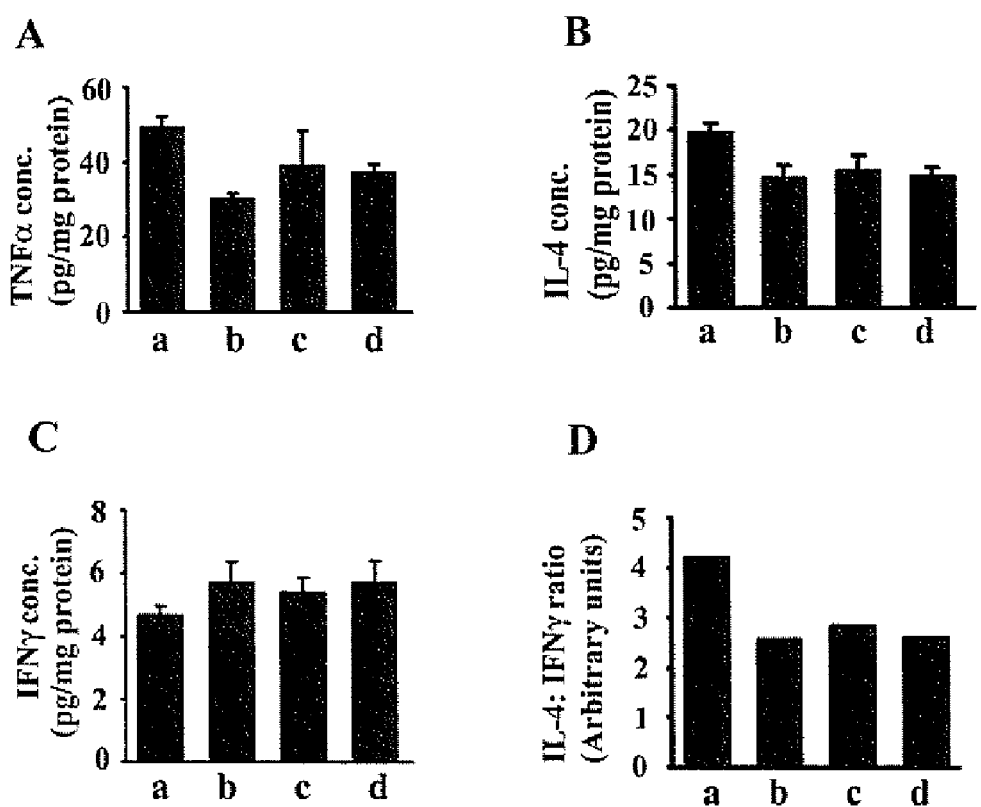
FIG. 9 represents Modulation of TNFα (A), IL-4 (B), IFN-γ (C) in Sephadex LH-20 induced airway inflammatory model of Sprague-Dawley rats supplemented with composition-1. Bar diagrams represent the Th1 and Th2 cytokines in lung tissue protein lysates. a, CMC control; b, Montelukast (5 mg/kg body wt.); c, Composition 1 (100 mg/kg body wt.); d, Composition 1 (200 mg/kg body wt.). Each bar represents mean±SD (n=6). Panel D, bar diagrammatic presentation of the ratio of IL-4 and IFN-γ in each group, as indicated.
Figure 10:
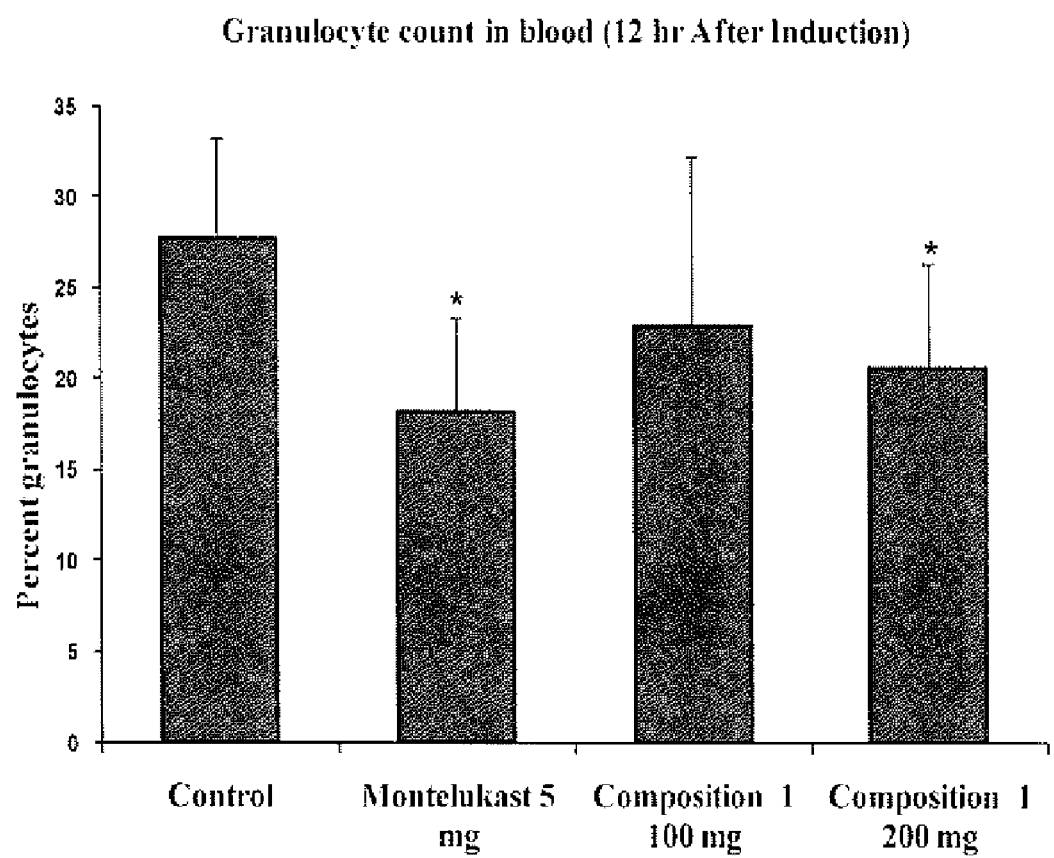
FIG. 10 Illustrates Bar diagrammatic representations of granulocyte percentage in whole blood after 12 hours after sephadex challenge. The bars represent, control, montelukast 5 mg/kg, Composition-1 100 mg/kg and composition-1 200 mg/kg. Each bar represents mean±SE. N=6, *: p<0.05.
Figure 11:
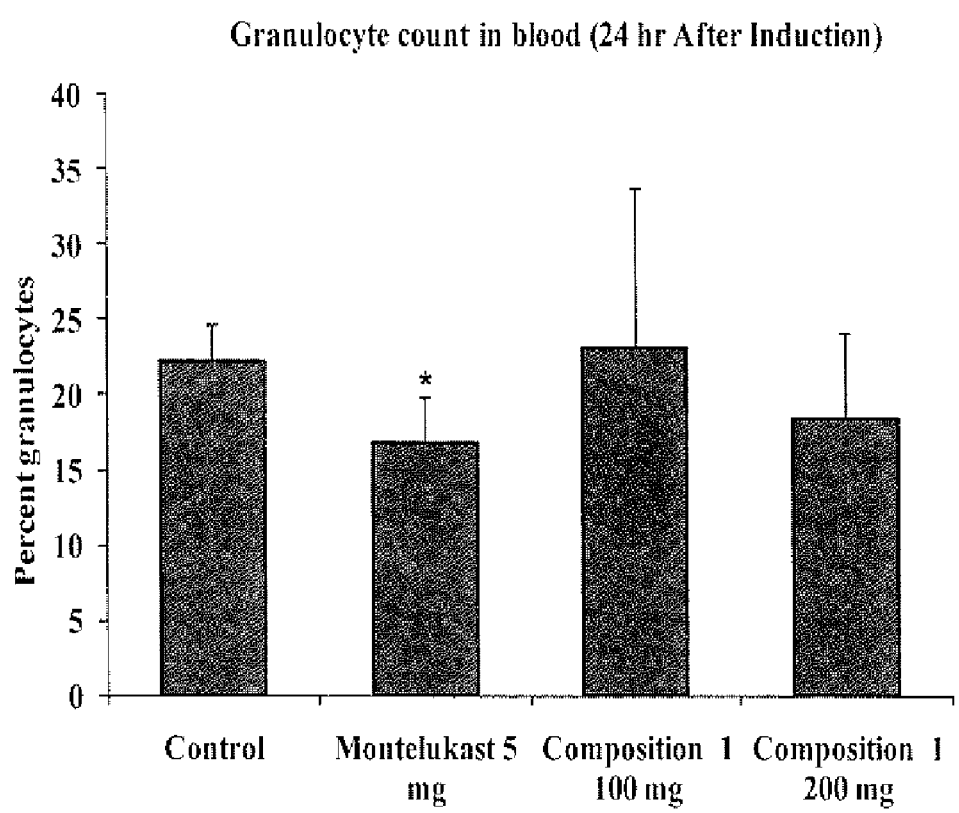
FIG. 11 Illustrates Bar diagrammatic representations of granulocyte percentage in whole blood, at 24 hours after sephadex challenge. The bars represent, control, montelukast 5 mg/kg, Composition-1 100 mg/kg and composition-1 200 mg/kg. Each bar represents mean±SE. N=6, *: p<0.05.
Figure 12:
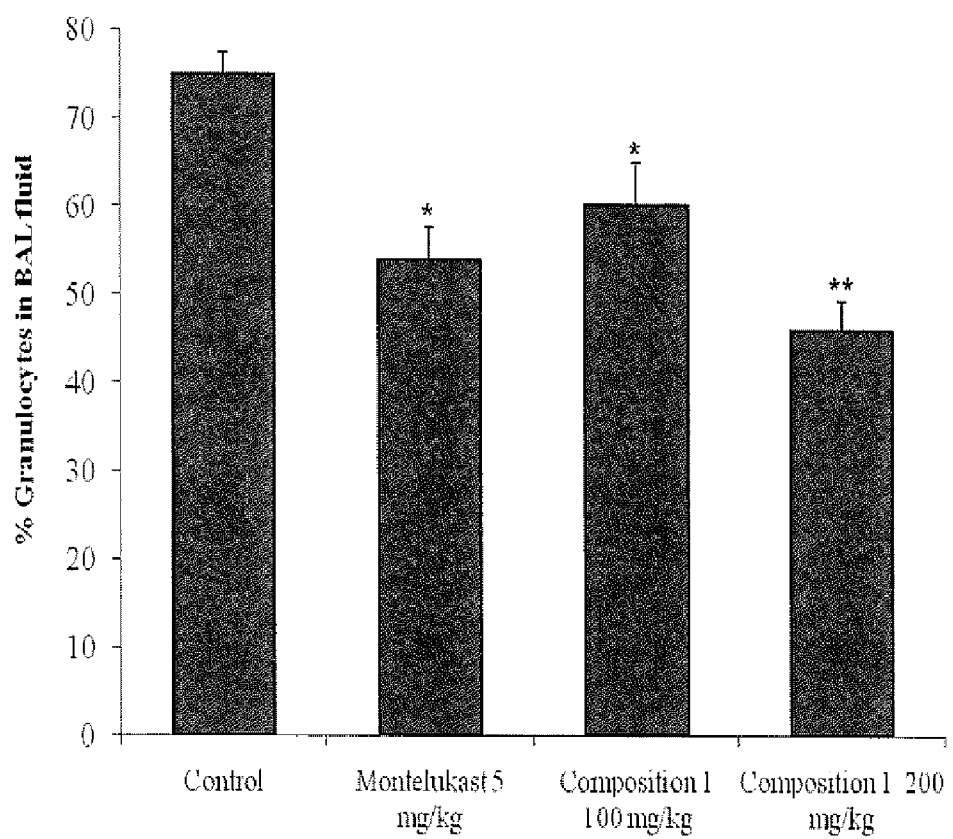
FIG. 12 Illustrates Bar diagrammatic representations of granulocyte percentage in BAL fluid, at 48 hours after sephadex challenge. The bars represent, control, montelukast 5 mg/kg, composition-1 100 mg/kg and composition-1 200 mg/kg. Each bar represents mean±SE. N=6, *: p<0.05 and **: p<0.01.

The induction of airway inflammation in Sprague-Dawley rats through intratracheal instillation of Sephadex as a suspension in sterile saline for 3 days significantly elevated granulocyte count in blood and Bronchoalveolar Lavage (BAL) fluid. However, the treatment with composition-1 potently ameliorated all the parameters towards the normal values. The data revealed statistically significant and dose related efficacy of composition-1 in various parameters tested, in comparison to control group (Vehicle). Estimation of biomarkers revealed that composition-1 can significantly inhibit the elevated TNF-α and IL-4 in the lung tissue samples (FIGS. 9A and 9B). The composition-1 also enhanced the IFNγ levels in the lung tissue of asthma induced animals (FIG. 9C). The composition-1 supplemented rats also showed significant improvement in Th2/Th1 cytokine balance (IL-4 vs. IFNγ ratio) and the effect is comparable with the rats treated with Montelukast (FIG. 9D). Statistically significant reduction of granulocytes in peripheral blood was observed in the groups supplemented with various doses of composition-1 (FIGS. 10 and 11) when compared to the control. However, the 200 mg treated group exhibited statistically significant efficacy. Composition-1 exhibited dose dependent reduction in percent granulocyte in Bronchoalveolar Lavage (BAL) fluid (FIG. 12). However, the 200 mg treated group exhibited statistically significant and comparable efficacy with Montelukast 5 mg/kg treated group. Composition-1 also exhibited dose dependent and highly significant reduction in percent eosinophils in peripheral blood (FIG. 13).

Figure 13:
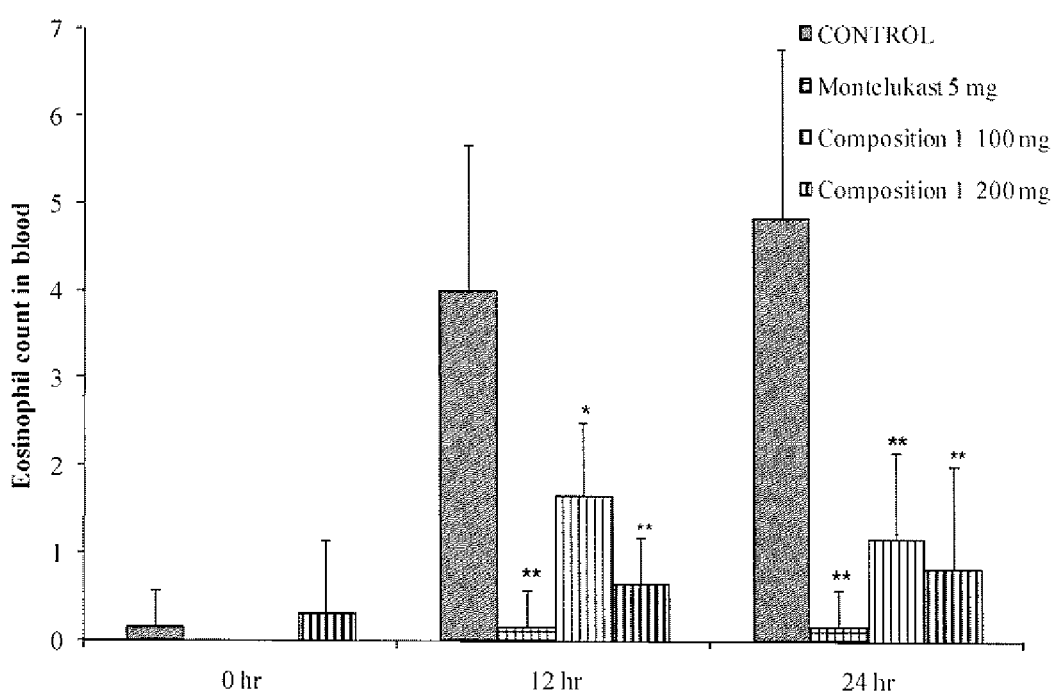
FIG. 13 Illustrates Bar diagrammatic representations of Eosinophil percentage in peripheral blood smears at 0, 12 and 24 hours after sephadex challenge. The bars represent, control, montelukast 5 mg/kg, Composition-1 100 mg/kg and composition-1 200 mg/kg. Each bay represents mean±SE. N=6, *: p<0.05 and **: p<0.01.

In summary, both doses of composition-1 supplementation reduced airway inflammation as evidenced by reduction in granulocytes infiltrated into BAL fluid and reduction of granulocytes (FIGS. 10, 11 and 12) and reduction of eosinophil percentages in peripheral blood smears (FIG. 13). In addition, significant reduction of pro-inflammatory cytokine and improvement in altered Th2/Th1 balance further substantiates the protective efficacy of the composition-1.

These observations suggest that 5-Loxin or the compositions containing 5-Loxin possess potential application for the prevention, treatment and control of TNF-α, aP2, FLAP and CysLT1 mediated diseases such as inflammation and asthma.

More importantly, the combined supplementation of 5-Loxin and extracts of *Aegle marmelos*, or optionally with one or more of extracts of *Zingiber officinale* and *Garcinia mangostana* provide potent anti-asthma activity.

Various exemplary embodiments of the invention provide herbal pharmaceutical or dietary supplement compositions with potent anti-inflammatory activity, especially anti-asthma activity. These compositions comprise a *Boswellia serrata* extract or fraction selectively enriched in 3-O-acetyl-11-keto-β-boswellic acid (AKBA), and at least one extract, fraction, or pure isolate derived from *Aegle marmelos*.

Various exemplary embodiments of the invention provide herbal compositions as a pharmaceutical or dietary supplement. These herbal compositions have potent anti-inflammatory and anti-asthma activity. The herbal compositions described in the current application comprise 5-Loxin and extracts of *Aegle marmelos* optionally along with one or more ingredients selected from the extracts/fractions/pure isolates of *Zingiber officinale* and *Garcinia mangostana*. These compositions further contain optionally pharmaceutically or dietetically acceptable additives or excipients.

The compositions comprising 5-Loxin and extracts of *Aegle marmelos* combined with one or more of the known anti-inflammatory or anti-asthma or immune modulating herbal extracts or fractions are also being considered.

Another embodiment of the invention provides inhibition of adipocyte fatty acid-binding protein (ap2) expression and/or inhibition of 5-Lipoxygenase Activating Protein (FLAP) expression and/or inhibition of Cysteinyl Leukotriene (Cys LT)-1 receptor expression by the compositions comprising *Boswellia serrata* extract or fraction selectively enriched in 3-O-acetyl-11-keto-β-boswellic acid (AKBA) and extract(s) or fraction(s) or pure isolate(s) derived from *Aegle marmelos*.

In various exemplary embodiments of the invention, the anti-asthma compositions comprising *Boswellia serrata* extract enriched in AKBA and extract(s) or fraction(s) derived from *Aegle marmelos* (Bael) fruit extract optionally along with one or more ingredients selected from *Zingiber officinale* and *Garcinia mangostana* may further optionally be combined with one or more of the known anti-inflammatory or anti-asthma or immune modulating herbal extracts or fractions are also being considered.

In another embodiment of the invention, the known anti-inflammatory and anti-asthma extracts or fractions include those derived from but not limited to *Achyranthes aspera, Annoa squamosa, Anogeissus latifolia, Bauhinia purpurea Boerhaavia diffusa, Calotropis gigantean, Cassia fistula, Chloroxylon swietenia, Cressa cretica, Curculigo orchioides, Cynodon doctylon, Datura metel, Euphorbia hirta, Evolvulus alsinoides, Ficus religiosa, Garuga pinnata, Justicia adhatoda, Madhuca latifolia, Morinda pubescens, Moringa*

*oleifera, Ocimum basilicum, Ocimum tenuiflorum, Pegularia daemia, Phyllanthus emblica, Piper longum, Piper nigrum, Pistacia integerrima, Prosopis julifera, Quercus infectoria, Randia dumetorum, Solanum surattense, Terminalia chebula, Tinospora malabarica, Trianthema portulacastrum, Tribulus terrestris, Tylophora Indica, Vitex negundo* and *Wrightia tinctoria.*

In further embodiments of the invention, the known immune modulating herbal agents include those derived from but not limited to *Centella asiatica*, Rehmannia, Astragalus, Echinaceae, Gynostemma, Glycerrhiza, Curcuma, *Prunella vulgaris, Scutellaria barbata, Cannabis sativa, Ganoderma lucidum*, and *Glycine max*/Soy isoflavones and/or their mixture thereof.

In various exemplary embodiments, the 3-O-acetyl-11-keto-beta-boswellic acid (AKBA) concentration in the enriched extracts and/or enriched fractions of *Boswellia serrata* varies from 10% to 99%, preferably 20% to 60% and more preferably 25% to 45%.

In certain embodiments, the percentage of *Boswellia serrata* extract enriched in 3-O-acetyl-11-keto-β-Boswellic acid in the composition varies from 1-95% and percentage of the extract of *Aegle marmelos* varies from 5-95%, based on the total weight of the extracts or fractions.

In another embodiment, the percentage of the enriched *Boswellia* extract(s) or fraction(s) obtained from *Boswellia serrata* varies in the range of 1-75% and the extract(s) or fraction(s) of *Aegle marmelos* varies in the range of 5-75%, the extract(s) of *Zingiber officinale* varies in the range of 1-50% and extract(s) of *Garcinia mangostana* varies in the range of 1-50%, based on the total weight of the extracts or fractions.

Various exemplary embodiments of the invention provide a method of treatment using the composition in humans or animals in need thereof, wherein the method comprises supplementing the said humans or animals with an effective amount of a composition comprising:
i) an effective amount of an enriched *Boswellia* extract containing at least 10% by weight of 3-O-acetyl-11-keto-β-Boswellic acid (5-Loxin) along with one or more ingredients selected from *Aegle marmelos, Zingiber officinale* and *Garcinia mangostana;*
ii) optionally combined with one or more known anti-inflammatory or anti-asthma or immune modulating herbal extracts or fractions; and
iii) further optionally combined with one or more pharmaceutically or dietetically acceptable additives or excipients.

Various exemplary embodiments of the invention provide the usage of the compositions for various pathological conditions including but not limited to inflammatory diseases, respiratory disorders like Asthma, allergic rhinitis, hay fever, Type-1 hypersensitivity, mild allergies, Osteo arthritis, Arthritis, Immuno modulation, Alzheimer's disease, Crohn's disease, topical diseases of skin like eczema and psoriasis and several other diseases associated or related thereof.

In yet another embodiment the invention provides compositions further comprising optionally effective amounts of pharmaceutically or dietetically acceptable anti-oxidants, adaptogens, anti-diabetic agents, bio-protectants, bioavailability enhancers and trace metals or mixtures thereof to form a formulation.

In various exemplary embodiments of the invention, the administration of the composition can be administered orally, parenterally, nasally, rectally, vaginally, transdermally, occu-larly or through any other suitable route. The composition can also be administered by inhalation, including inhalation from a nebulizer.

In various exemplary embodiments of the invention, the composition is provided as a pharmaceutical or dietary supplement dosage form suitable for oral administration. Dosage forms suitable for oral administration include tablets, soft capsules, hard capsules, pills, granules, powders, emulsions, suspensions, sprays, syrups and pellets. In various other embodiments of the invention, the composition is provided as a pharmaceutical dosage form suitable for parenteral administration such as liquid formulations for administration as drops or by injection, or as solid or semisolid dosage forms for suppositories.

In another embodiment, the invention provides the nutritional or dietary compositions in the form of foods or beverages. These foods or beverages comprise various exemplary embodiments of the inventive compositions containing an enriched *Boswellia* extract; and an effective amount of a second extract selected from the group consisting of an extract of *Aegle marmelos*, an extract of *Zingiber officinale*, an extract of *Garcinia mangostana*, and mixtures thereof. These foods or beverages can be prepared or provided as cereals, baby foods, healthy foods, or food for specified health uses such as solid food like chocolate or nutritional bars, semisolid food like cream or jam, or gel; and also as beverages. Specific and non-limiting examples of such food or beverage items include refreshing beverages, lactic acid bacteria beverages, drops, candies, chewing gum, chocolate, gummy candy, yoghurts, ice creams, puddings, soft adzuki bean jellies, jellies, cookies and the like.

In another embodiment of the invention, administration is done to a mammal or animal in need thereof in the form of effective formulation or beverage or food in a range from 0.01 to 500 mg/kg body weight/day.

The amount of composition that will be effective in the treatment of a particular disorder or condition will depend on the nature of the disorder of the condition, which can be determined by standard clinical techniques. In addition, the in vitro and in vivo assays may optionally be employed to help identify optimal dosage ranges. The precise dose to be employed in the formulation will depend on the route of administration, and the seriousness or advancement of the diseased condition, and should be decided according to the practitioner and each patient's circumstances. Effective dosages may be extrapolated from dose response curves derived from in vitro or animal model test systems. For example, an effective amount of compositions according to various embodiments of the invention is readily determined by administering graded doses of the composition and observing the desired effect.

The following examples, which include preferred embodiments, will serve to illustrate the practice of various embodiments of this invention, using appropriate doses/units of the selected individual ingredients for preparing the compositions. It is being understood that the particulars shown are by way of example and for purpose of illustrative discussion of preferred embodiments of the invention. These illustrations are not to limit the scope of the invention.

Example 1

A composition-1 was prepared by mixing unit doses of the following components: 5-Loxin (1 g) and (*Aegle marmelos*) Bael fruit ethanol extract (1 g).

Example 2

A composition-2 was prepared by mixing unit doses of the following components: 5-Loxin (1 g) and (*Zingiber officinale*) Ginger extract (1 g).

Example 3

A composition-3 was prepared by mixing unit doses of the following components: 5-Loxin (1 g) and *Garcinia mangostana* extract (1 g).

Example 4

A composition-4 was prepared by mixing unit doses of the following components: 5-Loxin (1 g), Bael alcohol extract (1 g) and ginger, hydroalcohol extract (1 g).

Example 5

A composition-5 was prepared by mixing unit doses of the following components: 5-Loxin (1 g) and Bael fruit ethanol extract (2 g).

Example 6

A composition-6 was prepared by mixing unit doses of the following components: 5-Loxin (1 g) and Ginger extract (2 g).

Example 7

A composition-7 was prepared by mixing unit doses of the following components: 5-Loxin (1 g) and Ginger extract (0.5 g).

Example 8

A composition-8 was prepared by mixing unit doses of the following components: 5-Loxin (1 g), Bael fruit ethanol extracts (1 g) Ginger extract (1 g) and *Garcinia mangostana* extract (1 g).

Example 9

A composition-9 was prepared by mixing unit doses of the following components: 5-Loxin (1 g), Bael fruit ethanol extract (1 g) and *Garcinia mangostana* extract (1 g).

Example 10

A composition-10 was prepared by mixing unit doses of the following components: 5-Loxin (1 g), Bael fruit ethanol extract (0.5 g) and excipient (0.5 g).

Example 11

Down-regulation of aP2 protein expression in THP-1 cell line by 5-Loxin: Based on the existing information, we sought to assess the effect of 5-Loxin on aP2 expression in human monocytes-macrophage cells. 5-Loxin-induced aP2 protein expression was evaluated in cell based in vitro model. Briefly, THP-1 human monocyte-macrophage cells were pre-treated with either 1 µM montelukast, a leukotriene receptor antagonist or 10 µM Nordihydroguaiaretic Acid (NDGA), a non-selective lipooxygenase inhibitor or 5 µg/ml of 5-Loxin for 2 h and thereafter primed with LPS to induce the inflammatory response. The cellular proteins were extracted by cell lysis buffer and subjected to immuno-western blot to detect the modulation of expression of aP2 protein.

The data clearly shows that lipopolysaccharide (LPS) significantly induced aP2 in human monocytes-macrophage cells. The treatment of the cells with 5-Loxin and positive controls montelukast and NDGA significantly reduced the LPS elevated aP2 levels back to the normal base line values (FIG. 1A).

Similar experiment was also conducted on *Aegle marmelos, Zingiber officinale* and *G. mangostana* extracts. The outcome of the studies have established that 5-Loxin. *Aegle marmelos, Zingiber officinale* and *Garcinia mangostana* are superior as potential inhibitors of aP2 expression (FIGS. 1B and 1C). The comparative percentage inhibitions of aP2 expression by 5-Loxin, *Aegle marmelos, Zingiber officinale* and *G. mangostana* extracts are summarized in FIG. 1D.

Example 12

Inhibition of 5-Lipoxygenase, FLAP and Cysteinyl LT1 protein expression by 5-Loxin: The effect of 5-Loxin on the key intermediary proteins of arachidonic acid mediated inflammatory pathway was assessed in LPS induced-THP-1 human-monocyte-macrophage cells in vitro. Briefly, THP-1 human monocyte-macrophage cells were pre-treated with 10 µg/ml of 5-Loxin for 1 h and thereafter, the cells were primed with LPS for 2 h to induce the inflammatory response. The cellular proteins were extracted by cell lysis buffer and subjected to immuno-western blot to detect the modulation of expression of 5-Lipoxygenase, FLAP and Cysteinyl LT1 protein expressions. 5-Loxin significantly inhibited 5-Lipoxygenase, FLAP and Cysteinyl LT1 protein expression in LPS induced-THP-1 human-monocyte-macrophage cells as summarized in FIG. 2.

Example 13

Anti-asthma activity: Down-regulation of pro-inflammatory markers in Sephadex LH-20 induced airway inflammation in Sprague-Dawley rats by 5-Loxin®:

Rats were fed either with CMC or 5-Loxin at 50 mg/kg or at 100 mg/kg for 10 days. Thereafter, vehicle (saline, 1 ml/kg) or Sephadex LH-20 (5 mg/kg) was given via intrathoracic route. Sephadex was prepared as a suspension by soaking in sterile saline for 3 days. Animals were sacrificed 48 h after saline or Sephadex challenge: blood and lung tissue samples were collected from respective animals. Pro-inflammatory cytokines such as TNF-α and IL-4 were measured in serum and protein lysates prepared from lung tissues. TNF-α and IL-4 were measured quantitatively by specific and sensitive ELISA kits (R&D Systems, USA), by following protocol supplied by the vendor.

Figure 3:
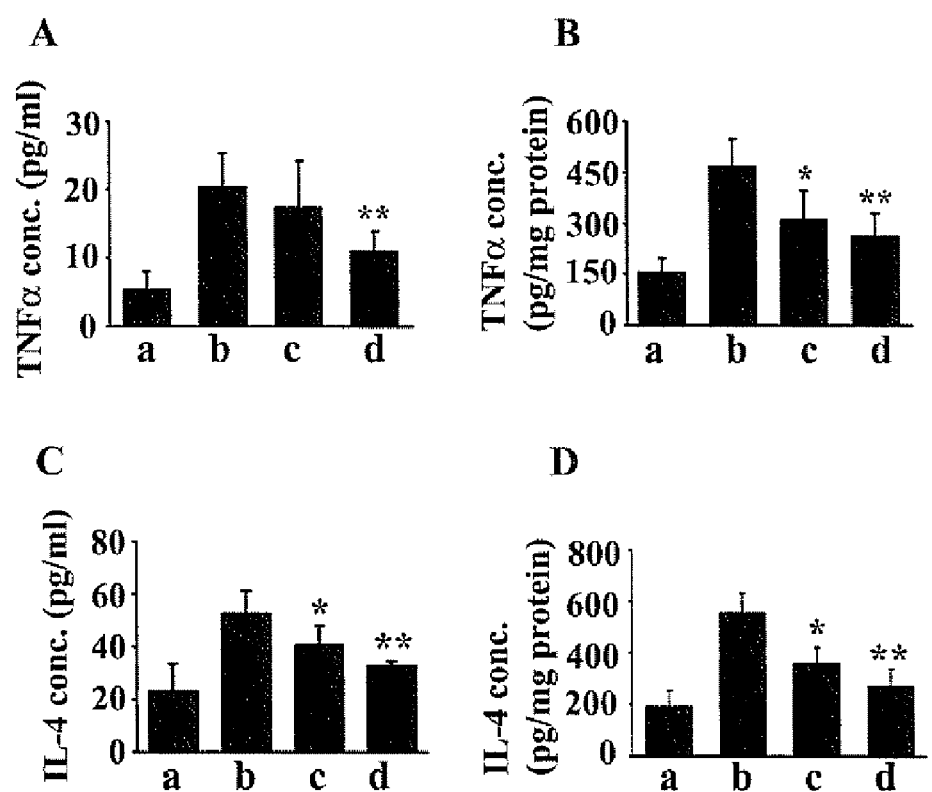
FIG. 3 represents in vivo anti-asthma efficacy of 5-LOXIN. The bar diagram represents the reduction of TNF-α (A & B) and IL-4 (C & D) levels in Sephadex LH-20 induced airway inflammatory model in Sprague-Dawley rats supplemented with 5-LOXIN®. The TNF-α and IL-4 concentrations were measured in serum (A & C) and lung tissue lysates (B & D) by specific antibody coated ELISA plates. Experiment includes (groups with saline (vehicle) inoculated in naïve animals (a), Sephadex inoculated in CMC (b), 50 mg/kg 5-Loxin® (c) and 100 mg/kg 5-Loxin® (d) supplemented rats, respectively. Each bar represents mean±SD (n=6). * and ** represents $P<0.05, P<0.01$ (vs. Sephadex challenge in CMC fed group), respectively.

5-Loxin significantly inhibited both serum and lung tissue TNF-α and IL-4 levels in the animal model (FIG. 3). As one can see from the following figure, the TNF-α and IL-4 levels were highly increased in the Asthma induced models (b), compared to the control animals (a). However, the 5-Loxin treated groups of animals (c and d) showed significantly reduced TNF-α and IL-4 levels. Most importantly there is a dose relation between 50 mg/kg 5-Loxin and 100 mg/kg 5-Loxin groups.

Example 14

Synergistic inhibition of aP2 protein expression by compositions-1 and 2 in THP-1 human monocyte-macrophage cells: The experimental procedure described in example 11 repeated with composition-1 comprising 5-Loxin and bael and composition-2 comprising 5-Loxin and ginger and evaluated the inhibition of aP2 expression with individual compositions. The composition-1 and 2 significantly inhibited the LPS induced aP2 expression in human monocytes-macrophage cells. Composition-1 and 2 also exhibited synergistic anti-aP2 expression activity and showed potent inhibitory activity compared to those of the individual ingredients as shown in FIGS. 4 and 5.

Example 15

Synergistic inhibition of 5-Lipoxygenase, FLAP and Cysteinyl LT1 protein expressions by Composition-1: The effect of Composition-1 on the key intermediary proteins of arachidonic acid mediated inflammatory pathway was assessed in LPS induced-THP-1 human-monocyte-macrophage cells in vitro. Briefly, THP-1 human monocyte-macrophage cells were pre-treated with 10 µg/ml of Composition-1 or 5-Loxin or Bael extract for 1 h and thereafter, the cells were primed with LPS for 2 h to induce the inflammatory response. The cellular proteins were extracted by cell lysis buffer and subjected to immuno-western blot to detect the modulation of expression of 5-Lipoxygenase, FLAP and Cysteinyl LT1 protein expressions. Composition-1 significantly inhibited 5-Lipoxygenase, FLAP and Cysteinyl LT1 protein expression in LPS induced-THP-1 human-monocyte-macrophage cells as summarized in FIG. 6. Composition-1 also showed synergistic activity and more potent inhibition compared to that of the individual ingredients, 5-Loxin and *Aegle marmelos*.

Example 16

Synergistic inhibition of 5-Lipoxygenase, FLAP and Cysteinyl LT1 protein expressions by Composition-2: The effect of Composition-2 on the key intermediary proteins of arachidonic acid mediated inflammatory pathway was assessed in LPS induced-THP-1 human-monocyte-macrophage cells in vitro. Briefly, THP-1 human monocyte-macrophage cells were pre-treated with 10 µg/ml of Composition-2 or 5-Loxin or ginger extract for 1 h and thereafter, the cells were primed with LPS for 2 h to induce the inflammatory response. The cellular proteins were extracted by cell lysis buffer and subjected to immuno-western blot to detect the modulation of expression of 5-Lipoxygenase, FLAP and Cysteinyl LT1 protein expressions. Composition-2 significantly inhibited 5-Lipoxygenase, FLAP and Cysteinyl LT1 protein expression in LPS induced-THP-1 human-monocyte-macrophage cells as summarized in FIG. 7. Composition-2 also showed synergistic activity and more potent inhibition compared to that of the individual ingredients, 5-Loxin and ginger.

Example 17

Anti-asthma activity of compositions-1, 2 and 3 in Sephadex LH-20 induced airway inflammation in Sprague-Dawley rats: In an in vivo study, the efficacy of composition-1, composition-2 and composition-3 in Sephadex LH-20 induced airway inflammation in Sprague-Dawley rats. Rats were fed either with Composition-1 or composition-2 or composition-3 at 50 mg/kg and 100 mg/kg for 10 days. The control group was treated with 0.5% CMC. Thereafter, vehicle (saline, 1 ml/kg) or Sephadex LH-20 (5 mg/kg) was given via intrathoracic route. Sephadex was prepared as a suspension by soaking in sterile saline for 3 days. Animals were sacrificed 24 h after saline or Sephadex challenge; blood and lung tissue samples were collected from respective animals. Pro-inflammatory cytokines such as TNFα and IL-4 were measured in protein lysates prepared from lung tissues. TNFα and IL-4 were measured quantitatively by specific and sensitive ELISA kits (R&D Systems, USA), following protocol supplied by the vendor. The IFN-γ concentration and the Th2 vs Th1 cytokines balance (IL-4/IFN-γ ratio) was also evaluated and the data is summarized in FIG. 8.

The TNF-α (8A) and IL-4 (8B) levels were highly increased in the Asthma induced models (2), compared to the control animals (1). Compositions-1, 2 and 3 significantly reduced both TNF-α and IL-4 in the treatment groups (3-7) compared to the untreated controlled group (2). Similarly, the IFN-γ concentration was significantly reduced in the asthma induced group (8C). These levels were enhanced in all the treatment groups supplemented with compositions-1, 2 and 3 at different dose levels. The compositions-1, 2 and 3 also improved Th2/Th1 cytokine balance (8D).

Example 18

Anti-asthma activity of compositions-1 in Sephadex LH-20 induced airway inflammation in Sprague-Dawley rats: The therapeutic efficacy of composition-1 at different doses was evaluated in Sephadex-induced airway inflammation model of Sprague-Dawley rats. Healthy Sprague Dawley rats were acclimatized for 7 days prior to the initiation of the study. All animals were fasted overnight at free access to water. Blood samples were drawn before initiation of treatment (baseline evaluation) and samples were submitted for hematology and DC. Animals were given daily oral treatment with composition-1 at doses 100 mg/kg body weight or 200 mg/kg body weight or standard or control for 10 days. Treatment was continued after induction till sacrifice. Blood samples were collected again on $10^{th}$ day of treatment and before induction of airway inflammation. All animal were treated intra-tracheally either with 20 mg/kg sephadex LH-20 in saline or saline alone (for Negative Control), blood samples were collected 12, and 24 and 48 hrs after sephadex induction. EDTA blood samples were submitted for hematology, plain bloods were centrifuge in refrigerated centrifuge and aliquots were stored in −80° C. for biomarker analysis. All animals were sacrificed 48 hrs after induction under euthanasia, Bronchoalveolar Lavage (BAL) fluids were collected by injecting 2 aliquots of 5 mL PBS in to lung. Lung tissue aliquots were collected and freezed using liquid nitrogen and stored at −80° C. for biomarker analysis. Additional lung sample was fixed in 10% buffered formalin and stored for possible histopathological examination. Cytokines such as TNF-α, IFN-γ and IL-4 were measured in protein samples isolated from lung tissue by cytokine ELISA kits (R&D Systems, USA). The results are summarized in FIG. 9. The percentage granulocytes in peripheral blood was measured and the data is summarized in FIGS. 10 and 11. BAL fluids were subjected for granulocyte count using a blood cell counter (Humcount). Sediment obtained from BAL fluid was smeared and differential counts were obtained by microscopy and the data is summarized in FIG. 12. The eosinophil count in blood was evaluated and summarized in FIG. 13.

We claim:
1. A composition for treating asthma, allergic rhinitis or hay fever comprising an effective amount of:
an enriched *Boswellia* extract containing from 10% to 99% by weight of 3-O-acetyl-11-keto-boswelic acid and a second extract component;
wherein said second extract component comprises an alcoholic or hydroalcoholic extract of *Aegle marmelos* fruit, and wherein said second extract component optionally comprises an extract selected from an extract of *Zingiber officinale*, an extract of *Garcinia mangostana* and mixtures thereof;

wherein said extract of *Aegle marmelos* fruit is present in an amount between 5% and 95% by weight based on the total weight of said *Boswellia* extract and said second extract component.

2. The composition of claim 1, wherein said enriched *Boswellia* extract contains 25% to 45% by weight of 3-O-acetyl-11-keto-β-boswellic acid.

3. The composition of claim 2, wherein said enriched *Boswellia* extract contains 30% by weight of 3-O-acetyl-11-keto-β-boswellic acid.

4. The composition of claim 1, wherein said composition optionally contains at least one pharmaceutically acceptable additive or excipient.

5. The composition of claim 1, wherein said composition further comprises at least one pharmaceutically acceptable additive or excipient.

6. The composition of claim 5, wherein said composition comprises a pharmaceutically acceptable additive and wherein said additive is selected from antioxidants, trace metals and mixtures thereof.

7. The composition of claim 1, wherein said composition is in an oral dosage form and wherein said dosage form is a tablet, a soft capsule, a hard capsule, a pill, a granule, a powder, an emulsion, a suspension, a spray, a syrup or a pellet.

8. The composition of claim 1, wherein said composition is in a parenteral dosage form and wherein said parenteral dosage form is selected from a liquid for injection, liquid drops or a suppository.

9. The composition of claim 1, wherein the composition is in the form of a nutritional supplement and wherein said nutritional supplement is a food or beverage.

10. The composition of claim 1, wherein said second extract component consists of said extract of *Aegle marmelos*.

11. The composition of claim 1, wherein the enriched *Boswellia* extract is present between 1% and 95% based on the total weight of the enriched *Boswellia* extract and the second extract component and wherein the second extract component comprises said extract of *Aegle marmelos* between 5% and 95% based on the total weight of the enriched *Boswellia* extract and the second extract component.

12. The composition of claim 1, wherein;
the enriched *Boswellia* extract is present between 1% and 95% based on the total weight of the enriched *Boswellia* extract and the second extract component; wherein the second extract component comprises the extract of *Aegle marmelos* between 5% and 75%, the extract of *Zingiber officinale* between 1% and 50% and the extract of *Garcinia mangostana* between 1% and 50%; and wherein the percentages of extracts in the second extract component are based on the total weight of the enriched *Boswellia* extract and second extract component.

13. The composition of claim 1, wherein said *Boswellia* extract and said second extract component are mixed in a ratio of from 1:2 to 2:1 by weight.

14. The composition of claim 1, wherein said second extract component comprises an extract of *Zingiber officinale*.

15. The composition of claim 1, wherein said second extract component comprises an extract of *Garcinia mangostana*.

16. A dietary supplement or pharmaceutical composition comprising the composition of claim 1.

17. A composition for treating asthma, allergic rhinitis or hay fever comprising an effective amount of:
an enriched *Boswellia* extract containing from 10% to 99% by weight of 3-O-acetyl-11-keto-boswelic acid and a second extract component;
wherein said second extract component comprises an ethanol or hydroalcoholic extract of *Aegle marmelos* fruit, and wherein said second extract component optionally comprises an extract selected from an extract of *Zingiber officinale* an extract of *Garcinia mangostana* and mixtures thereof;
wherein said extract of *Aegle marmelos* fruit is present in an amount between 5% and 95% based on the total weight of the enriched *Boswellia* extract and second extract component.

18. The composition of claim 1, wherein said second extract component is said extract of *Aegle marmelos* in combination with an extract of *Zingiber officinale*.

19. The composition of claim 1, additionally comprising a third extract, wherein said third extract is at least one of an anti-inflammatory or anti-asthma extract.

20. The composition of claim 1, further comprising an extract selected from the group consisting of extracts of *Aehyranthos aspora, Annona squamosa, Anogeissus latifolia, Bauhinia purpuroa, Boorhaavia diffusa, Calotivpis gigantoan, Cassia fistula, Chiolvxylon swietonia, Crossa erotica, Curculigo orehioidos, Cynodon doetylon, Datum mete], Euphorbia hirta, Evolvulus alsinoides, Ficus roligiosa, Garuga pinnata, Justieia adhatoda, Madhuea iatifolia, Morinda pubeseens, Moringa oleifera, Ocimum basilieum, Ocimum tenuiflorum, Pegularia daemia, Phyllanthus embliea, Piper longum, Piper nigrum, Pistaeia integerrima, Prosopis julifera, Quereus infoctoria, Randia dumetorum, Solanum surattense, Terminalia ehebula, Tinospora malabarica, Trianthema portulaeastrum, Tribulus terrestris, Tylophora indica, Vitex negundo, Wrightia tinctoria*, and combinations thereof.

21. A topical composition comprising an effective amount of:
an enriched *Boswellia* extract containing from 10% to 99% by weight of 3-O-acetyl-11-keto-boswelic acid and a second extract component;
wherein said second extract component comprises an alcoholic or hydroalcoholic extract of *Aegle marmelos* fruit, and wherein said second extract component optionally comprises an extract selected from an extract of *Zingiber officinale* an extract of *Garcinia mangostana* and mixtures thereof;
wherein said extract of *Aegle marmelos* fruit is present in an amount between 5% and 95% by weight based on the total weight of said *Boswellia* extract and said second extract component.

22. A method for treating asthma, allergic rhinitis or hay fever, comprising administering an effective amount of the composition of claim 1 to a person in need thereof.

23. The method according to claim 22, wherein administering comprises administering the composition between 0.01 to 500 mg/kg body weight/day.

24. The method of claim 22, wherein said second extract component consists of said extract of *Aegle marmelos*.

25. The method of claim 22, wherein said second extract component comprises said extract of an extract of *Zingiber officinale*.

26. The method of claim 22 wherein said second extract component comprises said extract of *Garcinia mangostana*.

27. The method of claim 19, wherein said second extract component is said extract of *Aegle marmelos* in combination with said extract of *Zingiber officinale*.

28. The method of claim 19 wherein;
the enriched *Boswellia* extract is present between 1% and 95% based on the total weight of enriched *Boswellia* extract and said second extract component; wherein the second extract component comprises: the extract of *Aegle marmelos* present in the composition between 5% and 75% the extract of *Zingiber officinale* between 1% and 50% and the extract of *Garcinia mangostana* between 1% and 50% and wherein the percentages of extracts in the second extract component are based on the total weight of the enriched *Boswellia* extract and second extract component.

29. A method of inhibiting adipocyte fatty acid-binding protein expression, comprising:
administering a composition according to claim 1 to a mammal exhibiting allergic airway inflammation.

30. The method of claim 29, wherein said second extract component consists of an extract of *Aegle marmelos*.

31. The method of claim 20, wherein said second extract component comprises said extract of *Zingiber officinale*.

32. The method of claim 29 wherein said second extract component comprises said extract of *Garcinia mangostana*.

\* \* \* \* \*